United States Patent [19]

Crudden

[11] Patent Number: 5,686,391
[45] Date of Patent: Nov. 11, 1997

[54] SARCOSINATES AS FLUAZIFOP-BUTYL ADJUVANTS AND ACTIVATORS

[75] Inventor: Joseph J. Crudden, Hudson, N.H.

[73] Assignee: Hampshire Chemical Corp., Lexington, Mass.

[21] Appl. No.: 504,273

[22] Filed: Jul. 19, 1995

[51] Int. Cl.$^6$ .................................................. A01N 43/40
[52] U.S. Cl. ........................ 504/258; 71/DIG. 1
[58] Field of Search ............... 71/DIG. 1; 504/25

[56] References Cited

U.S. PATENT DOCUMENTS

| | | | |
|---|---|---|---|
| 4,325,729 | 4/1982 | Rempfler et al. | 504/257 |
| 4,552,580 | 11/1985 | Aldwinckle | 71/DIG. 1 |

OTHER PUBLICATIONS

Croda Chemicals Ltd. Crodasinic "N–acyl sarcosine derivatives Wetting and dispersing agents for pesticide formulations". 2–pages, no date available.

Pesticide Dictionary (1–Page), 1995.

Pesticide Dictionary pp. C143 and C134, 1990.

The Agrochemicals Handbook, 3rd Ed., Unwin Bros. Ltd., Surrey (England), pp. AO535/Aug 91, AO971/Aug 91, 1991.

*Primary Examiner*—John Pak
*Attorney, Agent, or Firm*—Nields, Lemack & Dingman

[57] ABSTRACT

An adjuvant for Fluazifop-butyl, and preferably Fluazifop-P-butyl, having increased activity, lower irritancy and lower toxicity than conventional adjuvants. The adjuvant is $C_8$ to $C_{22}$ sarcosinate or sarcosinate salt, such as sodium cocoyl sarcosinate, sodium lauroyl sarcosinate, or combinations thereof, which is combined with Fluazifop-P-butyl and provides more effective activity.

16 Claims, No Drawings

SARCOSINATES AS FLUAZIFOP-BUTYL ADJUVANTS AND ACTIVATORS

BACKGROUND OF THE INVENTION

Fluazifop-butyl (butyl (RS) -2-[4-[[5-(trifluoromethyl)-2-pyridinyl]oxy]phenoxy]propanoate, or its enantiomer Fluazifop-P-butyl (butyl (R) -2-[4-[[5-(trifluoromethyl)-2-pyridinyl]oxy]phenoxy]propanoate), are represented by the following formula:

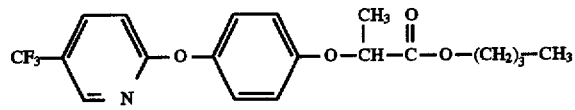

Both the racemic mixture and the enantiomer are selective herbicides, with the enantiomer being especially effective as a selective grass herbicide, exhibiting postemergence control of perennial and annual grass weeds over-the-top in cotton, soybeans and other broadleaved crops, including asparagus, carrots, dry bulb onions, spinach, sweet potatoes, and ornamentals. The enantiomer is sold commercially by Zeneca Ag Products under the tradename FUSILADE® 2000 or FUSILADE® DX.

Adjuvants are typically used in formulations to aid the operation or improve the effectiveness of the pesticide, herbicide, etc. The term includes wetting agents, spreaders, emulsifiers, dispersing agents, foaming adjuvants, foam suppressants, penetrants, and correctives. Adjuvants such as Valent X-77® Spreader are commonly used to enhance the performance of Fluazifop-P-butyl. However, Valent X-77® Spreader and other ethoxylated nonionic surfactants contain free ethylene oxide which may form 1,4 dioxane, a known carcinogen.

It is therefore an object of the present invention to provide Fluazifop-P-butyl adjuvants and activators which do not suffer from the drawbacks of the prior art.

It is a further object of the present invention to provide herbicide formulations with increased activity, lower irritancy and lower toxicity than conventional formulations.

SUMMARY OF THE INVENTION

The problems of the prior art have been overcome by the present invention, which provides an adjuvant for Fluazifop-butyl, and preferably Fluazifop-P-butyl, having increased activity, lower irritancy and lower toxicity than conventional adjuvants. The adjuvant is $C_8$ to $C_{22}$ sarcosinate or sarcosinate salt, such as sodium cocoyl sarcosinate, sodium lauroyl sarcosinate, or combinations thereof, which is combined with Fluazifop-P-butyl and provides more effective activity.

DETAILED DESCRIPTION OF THE INVENTION

Typically, sarcosinates are used in the form of their sodium, potassium or ammonium salt solution. N-Acyl sarcosinates are produced commercially by the Schotten-Baumann reaction of the sodium salt of sarcosine with the appropriate fatty acid chloride under carefully controlled conditions:

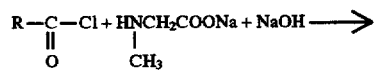

where R is typically a fatty acid of chain length $C_{10}$ to $C_{18}$, commonly made from lauric, coconut, palmitic, myristic or oleic acid. After the reaction is complete, the crude sodium salt is acidified to liberate the free fatty sarcosinic acid which is separated from the aqueous by-products. It then is neutralized to a salt form. Sarcosinates such as sodium lauroyl sarcosinate, sodium cocoyl sarcosinate and sodium myristoyl sarcosinate are commercially available under the trademark HAMPOSYL® from Hampshire Chemical Corp., as 30% active solutions in water.

The present inventor has found that $C_8$ to $C_{22}$ N-acyl sarcosinates, and in particular, sodium cocoyl and sodium lauroyl sarcosinate, are excellent adjuvants for Fuazifop-P-butyl. (The plus (P) enantiomer of Fuazifop-butyl has been found to contain the herbicidal activity of the racemic mixture, and has thus been isolated and formulated at half the concentration of the racemic mix. Accordingly, this enantiomer is preferred in the present invention. It should be understood by those skilled in the art, however, that although the following description refers to the (P) enantiomer, the racemic mixture could be used as well.) The sarcosinates are low in toxicity, irritancy, and when combined with Fuazifop-P-butyl, cause the same to exhibit increased activity.

Suitable salts of these sarcosinates that are useful in the present invention include monoethylamine; diethylamine; triethylamine; alkali metal salts, particularly sodium and potassium; isopropylamine; and ammonia or amino alcohols such as tris amino or 2-dimethylamino-2-methyl-1-propanol.

Preferably the 30% sarcosinate solutions are used so that the final concentration of sarcosinate in the formulation is from 0.1% to 3% (v/v), more preferably 0.5 to 1%. Higher concentrations of sarcosinates tend to be less effective, perhaps because excess surfactant tends to cause the herbicide to wash off the area of application.

The formulations are prepared by first mixing the sarcosinate with water, and then mixing the FUSILADE® herbicide with the resulting surfactant solution.

The invention is further illustrated by the following non-limiting examples.

EXAMPLE 1

Fuazifop-P-butyl was added to solutions of sodium cocoyl sarcosinate and sodium lauroyl sarcosinate. Valent X-77 was used as a control. Valent X-77 is 90% active and the sarcosinate solutions are 30% active. Four test systems and the control were tested for effectiveness in controlling Bermudagrass.

The Bermudagrass used in this experiment was established in 1985 and had been fertilized and mowed under normal practices until the treatments were applied. Following application of the treatments, unwanted weeds and grasses other than Bermudagrass were controlled with Quadmec thirty-three days after application; with MSMA 120 days after application; and with Trimec 333 days after application. The experimental area was not mowed until after the 120 days after treatment (DAT) ratings had been collected. The area was mowed prior to greenup. The area was fertilized with 68 units/A of nitrogen 350 days after application. The experimental area was irrigated on an as-needed basis.

Seven and fourteen date ratings of the effects were carried out. The Fuazifop-P-butyl was applied to Bermudagrass at 0.125 pounds active ingredient per acre, the Valent X-77 was added at 0.25% v/v and the sarcosinates at an equivalent active concentration, 0.75% v/v and at twice the level, 1.50%. The data are shown in Table 1 that follows.

At 7 days following application, only a yellowing effect was observed and no percent control could be rated (Table 1). Control was achieved at 14 DAT and the data appear to show that the addition of sodium cocoyl sarcosinate at 1.5% v/v and of sodium lauroyl sarcosinate at both 0.75% and 1.5% v/v increased the activity of FUSILADE® herbicide on common bermudagrass. At 31 days after application, the 0.75% v/v rate of sodium cocoyl sarcosinate and sodium lauroyl sarcosinate provided the best control, but all of the experimental adjuvants gave control superior to that of X-77.

TABLE 1

BERMUDAGRASS CONTROL WITH FUSILADE AND N-ACYL SARCOSINATE

Herbicide: Fusilade 2000  Weed: Bermudagrass
Use Rate: 0.125 pound/acre  Growth Stage: Post
Spray Volume: 22.86 gallons/acre  Soil Type: Sod
Control Adjuvant: X-77

| Adjuvant | Use Rate % V/V | % Control | | | | |
|---|---|---|---|---|---|---|
| | | 7 DAT | 14 DAT | 31 DAT | 121 DAT | 362 DAT |
| X-77 (90% active) | 0.25 | 15 | 40 | 15 | 0 | 0 |
| Na Cocoyl Sarcosinate (30% active) | 0.75 | 25 | 50 | 70 | 0 | 0 |
| Na Cocoyl Sarcosinate (30% active) | 1.50 | 30 | 65 | 50 | 0 | 0 |
| Na Lauroyl Sarcosinate (30% active) | 0.75 | 30 | 75 | 65 | 0 | 0 |
| Na Lauroyl Sarcosinate (30% active) | 1.50 | 25 | 70 | 40 | 0 | 0 |
| Check | | 0 | 0 | 0 | 0 | 0 |

EXAMPLE 2

Fuazifop-P-butyl was added to solutions of sodium cocoyl sarcosinate and sodium lauroyl sarcosinate. Valent X-77 was used as a control. Valent X-77 is 90% active and the sarcosinate solutions are 30% active. Four test systems and the control were tested for effectiveness in controlling Quackgrass.

The plots were 10'×60' laid out in a Quackgrass sod and the center 6' of each plot was sprayed, leaving 2' running checks on the outsides of each plot. Quackgrass ratings were visual estimates of % control based on a 0-100 scale, where 0=no control and 100=complete control.

Seven, fourteen, thirty, fifty-three and two hundred ninety date ratings of the effects were carried out. The Fuazifop-P-butyl was applied to Quackgrass at 0.125 pounds active ingredient per acre, the Valent X-77 was added at 0.25% v/v and the sarcosinates at an equivalent active concentration, 0.75% v/v and at twice the level, 1.50%. The data are shown below in Table 2.

The sample containing sodium cocoyl sarcosinate at 0.75% v/v resulted in slower initial activity than the sample used at a higher rate, but by 14 days after treatment (DAT) activity from the two rates was equal and remained equal for the remainder of the trial. Conversely, the low rate of sodium lauroyl sarcosinate resulted in faster initial activity than the higher rate. Activity for the two rates was equal by 14 DAT. By 290 DAT, only the sample with the higher rate of sodium lauroyl sarcosinate showed any continuing activity on Quackgrass.

TABLE 2

QUACKGRASS CONTROL WITH FUSILADE AND N-ACYL SARCOSINATE

Herbicide: Fusilade 2000  Weed: Quackgrass
Use Rate: 0.125 pound/acre  Growth Stage: Post
Spray Volume: 20 gallons/acre  Soil Type: Sod
Control Adjuvant: X-77

| Adjuvant | Use Rate % V/V | % Control | | | | |
|---|---|---|---|---|---|---|
| | | 7 DAT | 14 DAT | 30 DAT | 53 DAT | 290 DAT |
| X-77 (90% active) | 0.25 | 10 | 40 | 30 | 0 | 0 |
| Na Cocoyl Sarcosinate (30% active) | 0.75 | 8 | 30 | 25 | 10 | 0 |
| Na Cocoyl Sarcosinate (30% active) | 1.50 | 30 | 30 | 25 | 5 | 0 |
| Na Lauroyl Sarcosinate (30% active) | 0.75 | 30 | 15 | 15 | 0 | 0 |
| Na Lauroyl Sarcosinate (30% active) | 1.50 | 10 | 20 | 15 | 0 | 40 |

EXAMPLE 3

Fuazifop-P-butyl was added to solutions of sodium cocoyl sarcosinate and sodium lauroyl sarcosinate. Valent X-77 was used as a control. Valent X-77 is 90% active and the sarcosinate solutions are 30% active. Four test systems and the control were tested for effectiveness in controlling Quackgrass.

The plots were 10'×60' laid out in a Quackgrass, which was spring plowed, disked, and cultimulched. The center 6' of each plot was sprayed, leaving 2' running checks on the outsides of each plot. Quackgrass ratings were visual estimates of % control based on a 0-100 scale, where 0=no control and 100=complete control.

Seven, fourteen, thirty, and two hundred seventy-nine date ratings of the effects were carried out. The Fuazifop-P-butyl was applied to Quackgrass at 0.125 pounds active ingredient per acre, the Valent X-77 was added at 0.25% v/v and the sarcosinates at an equivalent active concentration, 0.75% v/v and at twice the level, 1.50%. The data are shown below in Table 3.

All of the additives showed similar rate response with Fuazifop-P-butyl. Substantial control was exhibited even as of 279 DAT.

TABLE 3

QUACKGRASS CONTROL WITH FUSILADE AND N-ACYL SARCOSINATE

| Herbicide: | Fusilade 2000 | Weed: | Quackgrass |
| --- | --- | --- | --- |
| Use Rate: | 0.125 pound/acre | Growth Stage: | Post |
| Spray Volume: | 20 gallons/acre | Soil Type: | Tilled |
| Control Adjuvant: | X-77 | | |

| | | % Control | | | |
| --- | --- | --- | --- | --- | --- |
| Adjuvant | Use Rate % V/V | 7 DAT | 14 DAT | 30 DAT | 279 DAT |
| X-77 (90% active) | 0.25 | 10 | 60 | 85 | 70 |
| Na Cocoyl Sarcosinate (30% active) | 0.75 | 10 | 55 | 90 | 70 |
| Na Cocoyl Sarcosinate (30% active) | 1.50 | 10 | 55 | 85 | 80 |
| Na Lauroyl Sarcosinate (30% active) | 0.75 | 10 | 50 | 80 | 60 |
| Na Lauroyl Sarcosinate (30% active) | 1.50 | 10 | 55 | 90 | 75 |

What is claimed is:

1. A herbicidal composition comprising a herbicidally effective amount of butyl-2-[4-[[5-(trifluoromethyl)-2-pyridinyl]oxy]phenoxy]propanoate and an activator comprising an N-acyl sarcosinate or a salt thereof having the formula:

$$RCON(CH_3)CH_2COOX$$

wherein R is $C_8$ to $C_{22}$ alkyl or alkenyl, and X is hydrogen, alkali metal, ammonium, $C_1$–$C_6$ alkylamine or an amino alcohol.

2. The herbicidal composition of claim 1, wherein said butyl-2-[4-[[5-(trifluoromethyl)-2-pyridinyl]oxy]phenoxy]-propanoate is butyl (R)-2-[4- [[5-(trifluoromethyl)-2-pyridinyl]oxy]phenoxy] propanoate.

3. The herbicidal composition of claim 1, wherein said N-acyl sarcosinate is selected from the group consisting of alkali metal salts of lauroyl sarcosinate, alkali metal salts of cocoyl sarcosinate, and a mixture of an alkali metal salt of lauroyl sarcosinate and an alkali metal salt of cocoyl sarcosinate.

4. The herbicidal composition of claim 2, wherein said N-acyl sarcosinate is selected from the group consisting of alkali metal salts of lauroyl sarcosinate, alkali metal salts of cocoyl sarcosinate, and a mixture of an alkali metal salt of lauroyl sarcosinate and an alkali metal salt of cocoyl sarcosinate.

5. The herbicidal composition of claim 1, wherein said activator is sodium lauroyl sarcosinate.

6. The herbicidal composition of claim 2, wherein said activator is sodium lauroyl sarcosinate.

7. The herbicidal composition of claim 1, wherein said activator is sodium cocoyl sarcosinate.

8. The herbicidal composition of claim 2, wherein said activator is sodium cocoyl sarcosinate.

9. A method of controlling weeds in grass, comprising applying to said grass an effective amount of a herbicidal composition comprising butyl-2-[4-[[5-(trifluoromethyl)-2-pyridinyl]oxy]phenoxy]propanoate and an activator comprising an N-acyl sarcosinate or a salt thereof having the formula:

$$RCON(CH_3)CH_2COOX$$

wherein R is $C_8$ to $C_{22}$ alkyl or alkenyl, and X is hydrogen, alkali metal, ammonium, $C_1$–$C_6$ alkylamine or an amino alcohol.

10. The method of claim 9 wherein said butyl-2-[4-[[5-(trifluoromethyl)-2-pyridinyl]oxy]phenoxy]propanoate is butyl (R)-2-[4-[[5-(trifluoromethyl)-2-pyridinyl]oxy] phenoxy]-propanoate.

11. The method of claim 9, wherein said activator is sodium lauroyl sarcosinate.

12. The method of claim 10, wherein said activator is sodium lauroyl sarcosinate.

13. The method of claim 9, wherein said activator is sodium cocoyl sarcosinate.

14. The method of claim 10, wherein said activator is sodium cocoyl sarcosinate.

15. The method of claim 9, wherein said activator is present in said herbicidal composition in a concentration of 0.75% or less.

16. The method of claim 10, wherein said activator is present in said herbicidal composition in a concentration of 0.75% or less.

* * * * *